(12) United States Patent
Abel et al.

(10) Patent No.: US 7,837,845 B2
(45) Date of Patent: Nov. 23, 2010

(54) SENSOR CARD FOR DETERMINING ANALYTES IN LIQUID OR GAS SAMPLES AND METHOD FOR PRODUCING SUCH A SENSOR CARD

(75) Inventors: Petra Abel, Friedberg (DE); Alexander Schrörs, Frankfurt (DE); Gabriele Chemnitius, Bad Homburg v.d.H (DE); Gerhard Mager, Bad Homburg-Obererlenbach (DE); Jürgen Häcker, Neu-Anspach (DE)

(73) Assignee: Fresenius Medial Care Deutschland GmbH, Bad Homburg (DE)

( * ) Notice: Subject to any disclaimer, the term of this patent is extended or adjusted under 35 U.S.C. 154(b) by 1111 days.

(21) Appl. No.: 10/992,193

(22) Filed: Nov. 17, 2004

(65) Prior Publication Data

US 2009/0321258 A1 Dec. 31, 2009

(30) Foreign Application Priority Data

Nov. 18, 2003 (DE) .............................. 103 53 938

(51) Int. Cl.
*G01N 27/26* (2006.01)
(52) U.S. Cl. .................................. 204/403.03; 204/409
(58) Field of Classification Search ................ 204/193, 204/194, 400, 403.01, 403.02, 403.03, 409
See application file for complete search history.

(56) References Cited

U.S. PATENT DOCUMENTS 4,225,410 A * 9/1980 Pace ............................ 204/412
4,454,007 A * 6/1984 Pace ............................ 205/778
4,871,441 A * 10/1989 Tsunekawa et al. ......... 204/409
5,018,527 A * 5/1991 Pfab et al. .................... 600/348

(Continued)

FOREIGN PATENT DOCUMENTS

DE 196 31 530 1/1998

(Continued)

OTHER PUBLICATIONS

Eggenstein et al., "A disposable biosensor for urea determination in blood based on an ammonium-sensitive transducer", Biosensors & Bioelectronics, vol. 14 (1999), pp. 33-41.

(Continued)

*Primary Examiner*—Nam X Nguyen
*Assistant Examiner*—J. Christopher Ball
(74) *Attorney, Agent, or Firm*—Kenyon & Kenyon LLP

(57) ABSTRACT

A sensor card for determining analytes in liquid and gas samples with films connected to one another in sheetlike fashion, namely a sensor film facing the sample with openings and a covering film remote from the sample with openings for electrical tapping, at least one sensor being provided and arranged between the sensor film and the covering film. There is provided between the sensor film and the covering film at least one intermediate film, in which cutouts are provided, the sensor being arranged in one of the cutouts. The sensor card provides a homogeneous thickness, which brings about a reliable sealing of the flow channels for the liquid sample if the sensor card is connected to a plate that partially forms the flow channels within the analysis system. Furthermore, the invention relates to a method for producing such a sensor card.

29 Claims, 3 Drawing Sheets

U.S. PATENT DOCUMENTS

| | | | |
|---|---|---|---|
| 5,405,510 A | 4/1995 | Betts et al. | |
| 5,700,360 A * | 12/1997 | Chan et al. | 205/778 |
| 5,830,337 A * | 11/1998 | Xu | 204/400 |
| 6,080,668 A * | 6/2000 | Lauffer et al. | 438/666 |
| 2002/0157947 A1 * | 10/2002 | Rappin et al. | 204/403.01 |
| 2003/0109807 A1 | 6/2003 | Knoll | |
| 2004/0211666 A1 * | 10/2004 | Pamidi et al. | 204/403.01 |

FOREIGN PATENT DOCUMENTS

| | | |
|---|---|---|
| DE | 197 47 875 | 5/1999 |
| DE | 199 29 264 | 1/2001 |
| WO | WO 99/20999 | 4/1999 |
| WO | WO 01/01120 | 1/2001 |
| WO | WO 02/097415 | 12/2002 |

OTHER PUBLICATIONS

Hampp et al., "Design and application of thick-film multisensors", Sensors and Actuators, vol. A31 (1992), pp. 144-148.

* cited by examiner

SENSOR CARD FOR DETERMINING ANALYTES IN LIQUID OR GAS SAMPLES AND METHOD FOR PRODUCING SUCH A SENSOR CARD

FIELD OF THE INVENTION

The present invention relates to a sensor card for determining analytes in liquid or gas samples with films connected to one another. Furthermore, the invention relates to a method for producing such a sensor card.

BACKGROUND

Sensor cards are used in measuring instruments or analysis systems in which a liquid or gas sample is subjected to a chemical analysis, it being possible to quantitatively determine different analytes in gaseous and liquid samples. Analysis systems of this type are increasingly being used in medical technology, process control and also foodstuffs and ecological analysis.

In this case, the analysis of parameters of body fluids in the context of point-of-care (POC) testing in the field of medical diagnosis constitutes a main area of use of these analysis systems. In the treatment of acutely and critically ill patients, it is important for the treating physicians to obtain precise information about the patients' physiological blood parameters, preferably in a rapid and simple manner. These blood parameters may include the blood gases ($pO_2$, $pCO_2$, pH), the electrolytes (Na, K, Ca, Cl), the conductivity of the blood and, derived therefrom, the hematocrit and the metabolites (glucose, lactate, urea, creatinine). In this case, the analysis location is increasingly being shifted away from the central laboratory personnel to those who also care for the patient. A considerable amount of time is thereby gained, which benefits a more rapid and more efficient treatment of the patient.

In developing the analysis systems used for this purpose, it is particularly important in this respect that the apparatuses can be operated simply and reliably and do not need complicated and time-consuming maintenance measures and the analysis costs per sample are kept as low as possible. There are currently known various conventional clinical analysis systems used for this objective. The conventional clinical analysis systems use predominantly electrochemical sensors for measuring the analytes. In this case, some systems use sensors of conventional design comprising electrode body, inner electrolyte and analyte-selective membrane, which last a long time but have to be maintained repeatedly in a time-consuming manner.

Recent analysis apparatuses are increasingly using maintenance-free planar sensors that can be mass-produced for instance by methods of thin-film and thick-film technology. A plurality of sensors, each of which can specifically determine an analyte, are applied on a substrate. In the flow cell, calibration solution and liquid samples are passed over the sensors in order to determine the analyte concentrations.

At the 17th International Symposium of the International Federation of Clinical Chemistry and Laboratory Medicine (IFCC), June 1998 in Nice, France, a new generation of sensor cards was presented which utilize the so-called double matrix membrane (DMM) technology. The conventional sensor cards with double matrix membranes have a sensor film with openings that face the liquid sample to be examined in the use position. A covering film is arranged on that side of the film which is remote from the liquid sample. Electrical conductor tracks made of silver/silver chloride are printed on the said covering film. The conductor tracks face the sensor film. Arranged between the sensor film and the covering film are carrier materials for ion-selective DMM sensors, which adjoin an opening in the sensor film and one of the films. The sensors are connected such that the openings in the sensor film are smaller than the sensor area, so that the edge of the opening presses down the edge of the sensor, which ultimately leads to a raising of the edge of the opening. The electrical tapping is effected directly at the conductor tracks, which, for this purpose, extend as far as the edge of the covering film, which is made larger than the sensor film, so that a part of the conductor track is not concealed by the sensor film and can be tapped.

Within the analysis system, the conventional DMM sensor card is connected in sheet-like fashion to a plate in which one or a plurality of grooves are situated. This connection gives rise to a flow channel for the liquid sample which is bounded by the wall of the grooves, on the one hand, and by the sensor film of the DMM sensor card, on the other hand. In this case, the openings in the sensor film point towards the flow channel, so that the sensors can be wetted with the liquid sample flowing through the flow channel. The conventional DMM sensor card has the disadvantage that it does not ensure reliable sealing of the flow channels within the plate.

Thus, there is a need for a sensor card for determining analytes in liquid samples which ensures a reliable sealing of the flow channels for the liquid sample, and also of specifying a method for producing such a sensor card.

SUMMARY OF THE INVENTION

The sensor card according to one embodiment of the present invention for determining analytes in liquid or gas samples has films connected to one another in sheet-like fashion. The film facing the liquid sample is designated as the sensor film and is provided with openings. In this connection, facing the liquid sample provides that the sensor film comes into contact with the liquid sample within the flow channels, e.g., the sensor card is later intended to be connected, as already described with reference to the prior art, in sheet-like fashion to the plate in which the grooves are situated. The sensor card furthermore has a covering film remote from the sample, e.g., the covering film does not come directly into contact with the sample. Furthermore, openings for electrical tapping are provided in the covering film. Furthermore, the sensor card has at least one sensor arranged between the sensor film and the covering film. Examples of appropriate sensors are potentiometric, amperometric or conductometric analyte-specific sensors. According to one embodiment of the present invention, at least one intermediate film is provided between the sensor film and the covering film. Cutouts are provided in the intermediate film, the sensor being arranged in one of the cutouts.

The sensor card according to one embodiment of the present invention has one advantage that it has a homogeneous thickness and a wavy form is avoided. This is attributable to the fact that the raising that arises as a result of the arrangement of the sensors between sensor film and covering film is compensated for by the intermediate film in whose cutouts the sensors are enclosed. A sensor card formed in such planar fashion can be fixed particularly simply and reliably in sheetlike fashion to the plate with grooves with which the sensor card forms the flow channels, thereby ensuring a high tightness of the flow channels. Moreover, the sensor card according to one embodiment of the present invention affords the advantages that it is made very thin, can hold very many sensors and can be produced cost effectively.

In a particularly advantageous embodiment of the sensor card according to the invention, the thickness of the intermediate film is chosen in such a way that it corresponds to or is greater than the thickness of the sensor. In the first case, an absolutely planar sensor card is created, while in the second case relatively small, inwardly pointing bulges may arise, in which case, with regard to the tightness of the flow channels, this may be more advantageous than projecting bulges such as occur in the case of the known DMM sensor card.

In order to enable an electrical tapping that is as simple and reliable as possible through the openings in the covering film, in a further preferred embodiment of the invention, the openings are filled with a cured electrically conductive paste. Carbon paste may preferably be involved in this case.

In a preferred embodiment of the sensor card, the sensor is formed as ion-selective sensor. The ion-selective sensor may, on the one hand, be electrically tapped via one of the openings in the covering film and may, on the other hand, be wetted with the liquid sample via one of the openings in the sensor film.

Advantageously, in a further embodiment of the present invention, the opening for electrical tapping of the ion-selective sensor is arranged offset with respect to the opening in the sensor film. In this case, offset is to be understood to mean that the opening in the covering film, in plan view of the sensor card, and the opening in the sensor film are arranged at a distance from one another, there preferably being no overlap of the two openings.

In a further embodiment of the sensor card according to the invention, the ion-selective sensor has a carrier material enclosed in the cut-out. An example of an appropriate carrier material is absorbent paper. In the region of the opening of the sensor film, the carrier material is activated or operated with an ion-selective reagent mixture. In this case, the reagent mixture completely fills the opening in the sensor film, so that the ion-selective sensor is reliably sealed relative to the sensor film.

In a particularly preferred embodiment, the carrier material of the ion-selective sensor has a conductive coating at its side facing the opening for electrical tapping. The conductive coating serves for the electrical connection of the ion-selective sensor and ensures reliable electrical tapping through the opening in the covering film.

In a particularly preferred embodiment of the present invention, the sensor film has printed-on electrical conductor tracks facing the intermediate film. Conductor tracks of this type may be applied for example by means of screen printing and likewise comprise carbon paste. By means of screen printing, it is also possible to produce particularly flat conductor tracks that likewise contribute to achieving the object according to the invention. The conductor tracks may be electrically connected in each case via the openings for electrical tapping and at least one of the cutouts in the intermediate film. In the case of this embodiment, it is possible to employ a through-plating, which is configured more simply and in a manner that saves more space than the lateral tapping at the known DMM sensor card.

In a further embodiment of the sensor card according to the present invention, the sensor is formed as a gas sensor. The gas sensor is in contact with a first conductor track and a second conductor track on the sensor film. Furthermore, the gas sensor can come into contact with the sample via one of the openings in the sensor film.

In a further embodiment of the sensor card according to the present invention, the gas sensor is a carbon dioxide sensor comprising a carrier film having a coating facing the sensor film, preferably an imprint made of silver/silver chloride and a pH-sensitive material.

In a further embodiment of the present invention, the gas sensor is an oxygen sensor. The oxygen sensor comprises a carrier film with layers of a material suitable as working electrode and of a material suitable as reference electrode, the layers being applied, preferably printed, on the carrier film, and facing the sensor film.

In accordance with a further advantageous embodiment of the present invention, the sensor is a conductivity sensor. The latter has two electrically conductive line sections which are spaced apart from one another and are printed on that side of the intermediate film which faces the sensor film. Like the conductor tracks, for example, the line sections may be applied by means of screen printing and comprise a dried carbon paste. One line section is in contact with a first conductor track on the sensor film and the other line section is in contact with a second conductor track on the sensor film. The conductivity sensors may be wetted with the liquid sample via openings in the sensor film and thereby be electrically conductively connected in order to determine the conductivity of the liquid sample.

In order to ensure sufficient ventilation, in an advantageous embodiment of the sensor card, a ventilation membrane is arranged in at least one of the cutouts in the intermediate film. The ventilation membrane adjoins a ventilation opening in the sensor film, on the one hand, and a ventilation opening in the covering film, on the other hand.

It may be desirable in the analysis systems to connect two mutually separate flow channels within the plate on which the sensor film is fixed by means of a narrow channel that is produced in the plate itself by means of a relatively high outlay. In order to produce such a channel, in a particularly preferred embodiment of the sensor card according to the invention, one of the cutouts in the intermediate film is formed in elongate fashion, the elongate cut-out being in flow connection with at least two separate openings in the sensor film. Consequently, through one of the openings in the sensor film, a liquid or a gas, e.g., a reagent solution, for example, may pass into the elongate cut-out in order to emerge from there again through the second of the two openings in the sensor film. This may be used for example for connecting a flow channel for a reagent solution to a flow channel for a liquid sample. A connection of the flow channels for reagent solution and liquid sample is to be provided for example when the inner electrolyte of a reference electrode, which may be made available in a bag, is intended to be fed to the sample channel during the measurements intermittently via the flow channel for the reagent solution.

In a particularly preferred embodiment of the sensor card according to the present invention, the two separate openings in the sensor film are likewise formed in elongate fashion and run transversely, preferably at right angles, with respect to the elongate cut-out in the intermediate film. This provides that the two elongate openings in the sensor film and the elongate cut-out in the intermediate film are also actually in flow connection as desired. Whereas in the case of punctiform openings in the sensor film it would be necessary to comply with small tolerances when laying the films one above the other, in order to ensure a flow connection, when there are elongate openings in the sensor film even relatively large displacements of the films with respect to one another are not significant since the elongate opening can overlie the elongate cut-out at a plurality of points. The production of the sensor card is thus simplified.

According to one embodiment of the present invention, a method for producing a sensor card for determining analytes in liquid or gas samples with films connected to one another in sheetlike fashion has the following method steps. First, provision is made of a sensor film with openings, a covering film with openings for electrical tapping and at least one intermediate film, in which cutouts are provided. Then, at least one sensor or the part of a sensor is arranged in one of the cutouts of the intermediate film. Finally, the films arranged one above the other are connected to one another in sheetlike fashion, the intermediate film being arranged between sensor film and covering film.

The method according to the invention provides several alternatives. For example, the finished sensor or only a part of a sensor that is still to be completed in a subsequent method step may be arranged in the cut-out of the intermediate film. Thus, instead of the finished sensor, it is also possible for only the carrier material of the sensor, which may already be provided with electrodes, to be inserted into the intermediate film. After the connection of the films, the carrier material is then activated or operated. The carrier material may comprise different materials. The activation or operation may be effected by applying one or a plurality of further materials serving for the activation or operation to the carrier material through the opening in the sensor film. The incorporation of a finished sensor has the advantage of simple production, while the incorporation of a part of a sensor that is still to be activated or operated has the advantage that the part of the sensor with the material to be applied for the activation or operation reliably seals the finished sensor with respect to the sensor film.

In a particularly preferred embodiment of the method according to the invention, at least one of the films, e.g., sensor film or covering film, is partially connected to the intermediate film in sheetlike fashion prior to arranging the sensor or the part of the sensor in one of the cutouts. Such a method enables the sensors to be arranged more simply within the cut-out in the intermediate film since the sensor is prevented from falling out by the partly fixed covering or sensor film.

In a further particularly advantageous embodiment of the present invention, both the sensor film and the covering film are partially connected to the intermediate film in sheetlike fashion prior to arranging the sensor or the part of the sensor in one of the cutouts. Besides the advantage mentioned in the above-described embodiment, this additionally has the advantage that it can be recognized whether the openings and cutouts in the films are arranged correctly with respect to one another prior to completing the connection.

A further embodiment of the method according to the present invention provides that, prior to providing the sensor film, conductor tracks are printed onto that side of the sensor film which is to face the intermediate film, preferably by screen printing. Screen printing is a reliable method that enables particularly flat conductor tracks to be produced.

In a further embodiment of the present invention, prior to providing the intermediate film, line sections are printed onto that side of the intermediate film which is to face the sensor film, preferably by screen printing. Screen printing is sought by production also on that side of the covering film which faces the intermediate film. In principle, it is possible to print onto both sides of the intermediate film and the inner sides of the covering film and sensor film. The connection of the films is preferably effected by adhesive bonding, hot lamination, heat welding or radio frequency welding.

Individual films or all films of the card may be locally omitted in order to enable further functions together with the surroundings of the sensor card and in order to enable an exact positioning of the sensor card relative to a plate with groove.

The sensor card may be positioned such that, if necessary, individual openings of the sensor film can be filled in order to activate or operate the sensors. For ion-selective sensors, it is possible to apply the corresponding ion-selective reagent mixtures, e.g., cocktails. The respective ion-selective reagent mixtures, e.g., cocktails, for the different ion-selective sensors are applied dropwise into the relevant openings onto the carrier material and dried. It is also possible for gas-permeable membranes for gas sensors to be applied by metering and dried. It is also possible for the functional layers to be applied directly to the sensor inlays prior to the films finally being joined together. Other or additional materials for the, activation or operation such as are used e.g. for biosensors may be applied analogously.

The sensor card can be adapted to the analytical tasks in a simple manner by the type and the number of the sensors that are integrated in its intermediate film being coordinated with the substances to be analysed. The construction of the sensor card is to be regarded as modular in this respect. Moreover, it is also possible to print further sensors directly onto the intermediate film instead of inserting them as sensor inlays into the cutouts of the intermediate film.

BRIEF DESCRIPTION OF THE DRAWINGS

The invention is explained further below according to an exemplary embodiment with reference to the accompanying figures.

DETAILED DESCRIPTION

Figure 1A:
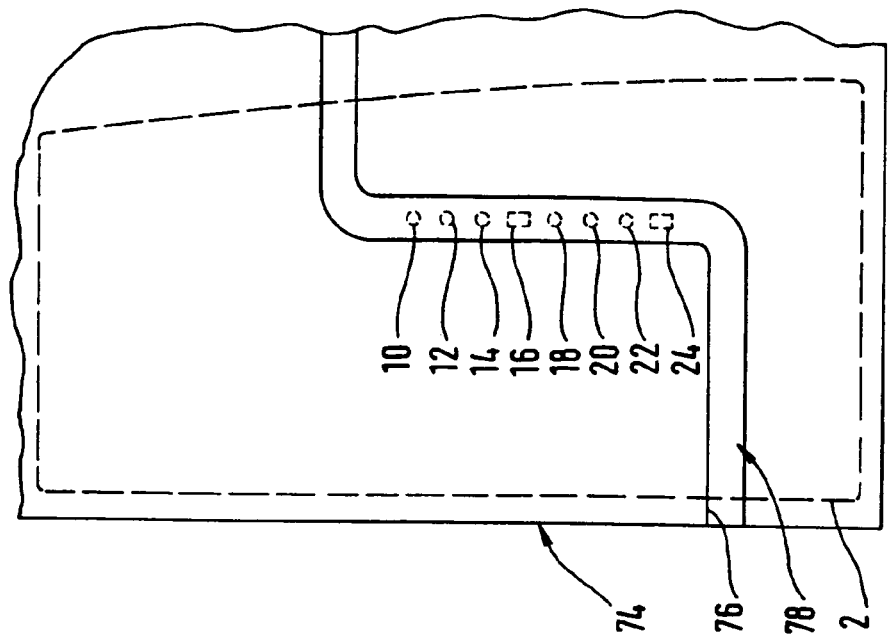
FIG. 1a shows a plan view of an arrangement with a sensor card and a patterned plate, according to one embodiment of the present invention.
Figure 1:
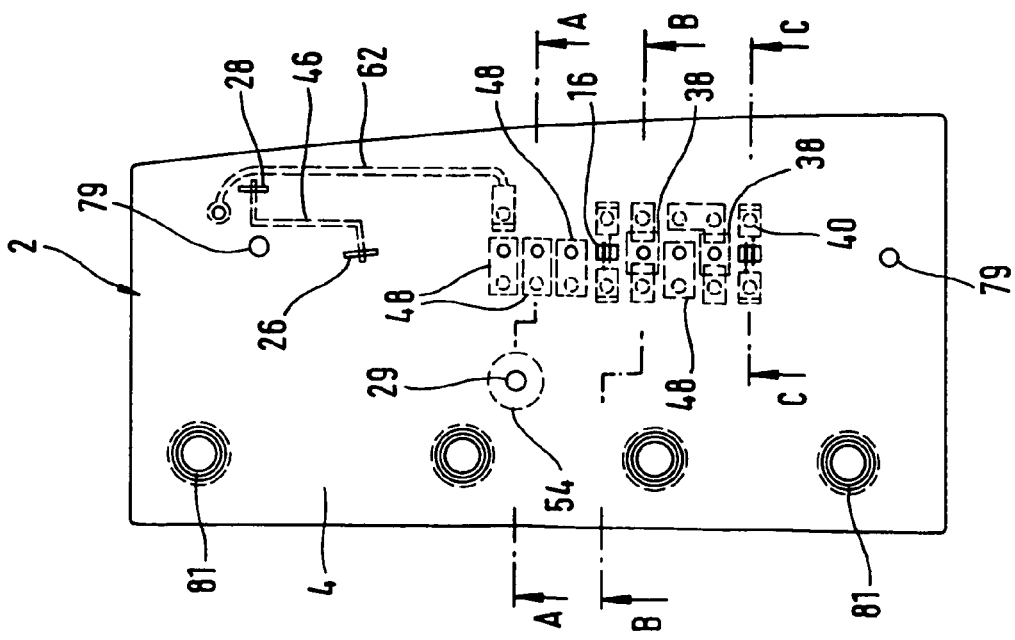
FIG. 1 shows a plan view of sensor card, according to one embodiment of the present invention.

FIG. 1 shows in plan view an embodiment of the sensor card 2 according to one embodiment of the present invention. The construction of the sensor card 2 will be explained in greater detail with reference to FIG. 2, for reasons of clarity.

The sensor card 2 has a sensor film 4 and a covering film 6, the sensor film 4, in the course of a measurement, facing the liquid sample (not illustrated) to be analysed, whereas the covering film 6 is remote from the liquid sample. An intermediate film 8 is arranged between the sensor film 4 and the covering film 6. In the present embodiment, the films 4, 6, 8 are polyester films that have a thickness of between 80 and 120 µm and are connected to one another in sheetlike fashion.

The sensor film 4 has a plurality of openings 10, 12, 14, 16, 18, 20, 22 and 24 arranged in a line. Furthermore, two elongate openings 26, 28 spaced apart from one another and also a ventilation opening 29 are provided in the sensor film 4. Furthermore, printed-on electrical conductor tracks (illustrated by broken lines) are provided on that side of the sensor film 4 which faces the intermediate film 8, in each case one conductor track 30 being arranged above the openings 16, 18, 20, 22 and 24 and in each case a further conductor track 32 being arranged below the openings 16, 18, 22 and 24. Furthermore, a further conductor track 34 for a reference electrode is arranged above the opening 10.

The intermediate film 8 has a plurality of cutouts 36, 38, 40, 42 and 44. Furthermore, an elongate cut-out 46 is provided. Ion-selective sensors 48 are arranged in the cutouts 36, which are formed in rectangular fashion in the case of the present embodiment, while gas sensors, namely an oxygen sensor 50 and a carbon dioxide sensor 52, are inserted into the cut-outs 38. A ventilation membrane 54 is provided within the annular cut-out 44.

Furthermore, two conductivity sensors 56 are arranged on the intermediate film 8, which conductivity sensors in each case have two electrically conductive line sections 58, 60, which are spaced apart from one another and are printed on the side facing the sensor film 4. Furthermore, an extended line section 62 functioning as reference electrode is printed on this side of the intermediate film 8.

A plurality of openings 64, 66 for electrical tapping and also a ventilation opening 68 are again provided in the covering film 6.

The sensor card 2 is connected to a plate 74 (FIG. 1a) that forms an exchangeable unit (disposable) with further components within the analysis system or the measuring instrument. For exact positioning of the sensor card 2 on the plate 74, positioning holes 79 are provided in the sensor card, pins provided on the plate engaging through the positioning holes.

The sensor card 2 is connected to the plate 74 in such a way that the sensor film 4 bears on the plate. The plate 74 has at least one laterally open channel 76, which may be formed by a groove. This creates a flow channel 78 for the liquid sample which is bounded by the wall of the channel 76 of the plate 74, on the one hand, and the inner side of the sensor film 4, on the other hand. In this case, the flow channel 78 leads along the openings 10, 12, 14, 16, 18, 20, 22 and 24 arranged in a line in the sensor film 4, so that the liquid or gas sample can come into contact with the sensors 48, 50, 52, 56 located behind.

The two separate elongate openings 26 and 28 that are spaced apart from one another in the sensor film 4 are in flow connection with a respective section of the elongate cut-out 46 in the intermediate film 8, so that liquids or gases, for example reagent solution as inner electrolyte of the reference electrode of the ion-selective sensors, or, if appropriate, also sample liquid can flow from one opening 26 or 28 through the elongate cut-out 46 to the other opening 28 or 26, respectively. The two elongate openings 26, 28 advantageously extend in each case transversely, preferably at right angles, with respect to the elongate cut-out 46 in the intermediate film 8, as is illustrated in FIG. 1. Furthermore, the sensor card has regions, 81 at which actuating members (not illustrated) act for opening liquid bags (not illustrated) which are provided in the disposable unit. In these regions 81, the sensor film 4 is thermoformed, while openings 82 are provided in the intermediate film 8 and the covering film 6. What is thereby achieved is that the actuating members that act at these regions of the sensor card do not exert any pressure on the sensor card as long as they are not actuated.

The functioning and also the advantages of the present embodiment will now be explained with reference to FIGS. 3 to 5.

Figure 3:
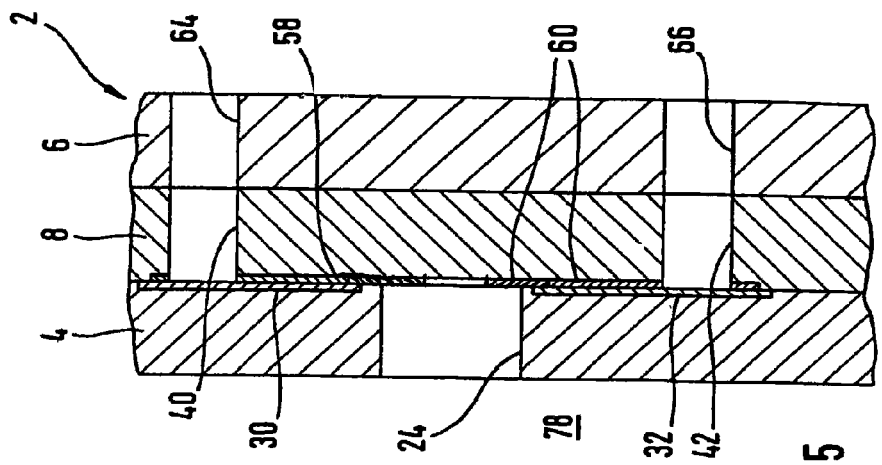
FIG. 3 shows a sectional view along the section line A-A from FIG. 1.

FIG. 3 shows the ion-selective sensor 48 arranged between the sensor film 4 and the covering film 6 and comprising a carrier material 48', which is activated or operated with an ion-selective reagent mixture (cocktail) 48" in the region of the opening 12. In this case, the ion-selective cocktail completely fills the opening and seats the sensor with respect to the sensor film.

The carrier material 48' of the ion-selective sensor 48 is arranged within the cut-out 36 in the intermediate film 8, so that the sensor card 2 is no thicker in the region of the ion-selective sensor 48 than in other regions in which no sensor is provided. For this purpose, the thickness of the intermediate film 8 corresponds to the thickness of the carrier material of the sensor. The sensor card thus has the advantage that it has a homogeneous thickness. A sensor card 2 formed in such planar fashion can be fixed particularly simply and reliably in sheetlike fashion to the plate with grooves with which the sensor card 2 forms the flow channels, thereby ensuring a high tightness of the flow channels. The same also applies correspondingly to the other sensors described later and also to the ventilation membrane 54 that is likewise illustrated in FIG. 3.

The ion-selective sensor 48 can be electrically tapped via the opening 66 assigned to the sensor 48 in the covering film 6, in order to forward corresponding signals to the evaluation unit (not illustrated) of the analysis system. Furthermore, the ion-selective sensor 48 has a conductive coating 70 at its side facing the opening 66 for electrical tapping, which coating simplifies the electrical tapping. On the other side, the ion-selective sensor 48 can be wetted with the liquid sample (not illustrated) in the region of the opening 12 in the sensor film 4.

As can be seen from FIGS. 3 and 1, the opening 12 in the sensor film 4 and the opening 66 for electrical tapping are arranged offset with respect to one another. The opening 66 for electrical tapping, like the other openings 64, 66 as well in the covering film, is filled with a cured electrically conductive paste 67, namely carbon paste, which facilitates the tapping and makes it more reliable. For reasons of clarity, the paste 67 has been indicated by way of example merely on the basis of the opening 66 in FIG. 3.

The ventilation membrane 54 is illustrated at the bottom of FIG. 3, the ventilation membrane being enclosed in the cut-out 44 in the intermediate film 8. The ventilation membrane 54 adjoins the ventilation opening 29 on the sensor film side and the ventilation opening 68 on the covering film side. Since the ventilation opening 68 serves for ventilation and not for electrical tapping, it is not filled with carbon paste. Like all sensors as well, the ventilation membrane 54 is made larger than the opening 29 assigned to it, so that it is reliably enclosed in the cut-out 44 in the intermediate film 8.

Figure 4:
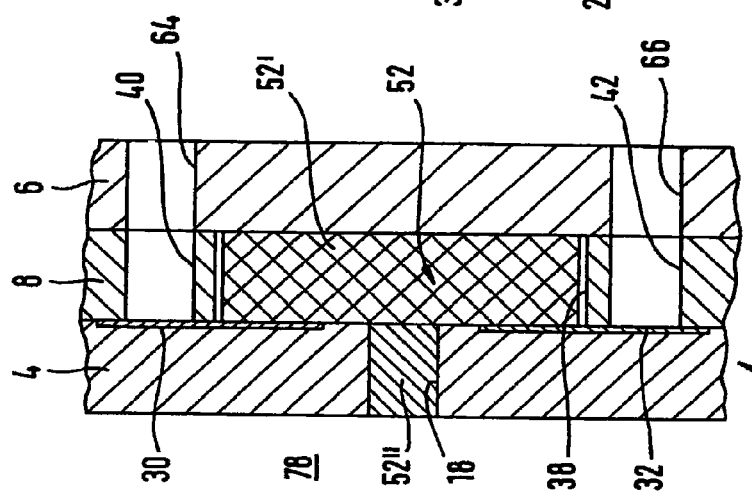
FIG. 4 shows a sectional view along the section line B-B from FIG. 1.

FIG. 4 shows the carrier material 52' of the carbon dioxide sensor 52 arranged between the sensor film 4 and the covering film 6. In this case, the carrier material 52' of the carbon dioxide sensor 52 is arranged within the cut-out 38 in the intermediate film 8, so that the advantages described with reference to FIG. 3 likewise occur with regard to the thickness of the entire sensor card 2. The carbon dioxide sensor 52 is in contact with the first conductor track 30 on the sensor film 4, on the one hand, and with the second conductor track 32 on the sensor film 4 on the other hand. The conductor track 30 can be electrically tapped via the opening 64 in the covering film 6 and the cut-out 40 in the intermediate film 8, while the conductor track 32 can be electrically tapped via the opening 66 in the covering film 6 and the cut-out 42 in the intermediate film 8. Mention is also made here of a through-plating. The cutouts 40 and 42 are also filled with carbon paste, which is not illustrated for the reasons mentioned above.

The carrier material 52' of the carbon dioxide sensor 52 has a coating facing the sensor film 4, preferably an imprint made of silver/silver chloride and a pH-sensitive material. As activation or operation, an inner electrolyte and gas-permeable membrane 52" are applied on the coating. The inner electrolyte and gas-permeable membrane 52" fill the opening 18 in the sensor film 4.

While the electrical tapping is effected from behind, that is to say via the covering film, the carbon dioxide sensor 52 can come into contact with the sample at its side facing the sensor film 4 through the opening 18 in the sensor film 4.

Figure 5:
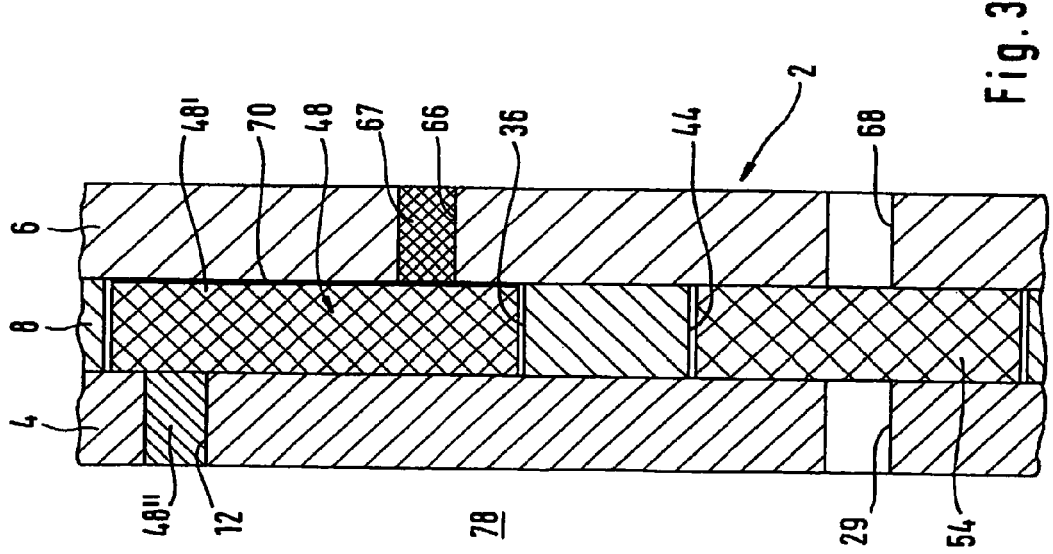
FIG. 5 shows a sectional view along the section line C-C from FIG. 1.

FIG. 5 shows the conductivity sensor 56 (FIG. 2) in cross section. In contrast to the two sensors described with reference to FIGS. 3 and 4, the conductivity sensor 56 is not formed as a sensor inlay, but rather comprises the line sections 58 and 60 described in the introduction which are printed on that side of the intermediate film 8 which faces the sensor film 4. In this case, one line section 58 is in contact with a first conductor track 30 situated on the sensor film 4, while the other line section 60 makes contact with a second conductor track 32 situated on the sensor film 4. The first conductor track 30 can be electrically tapped via the opening 64 in the covering film 6 and the cut-out 40 in the intermediate film 8, while the second conductor track 32 can be electrically tapped via the opening 66 in the covering film 6 and the cut-out 42 in the intermediate film 8. The cut-outs 40 and 42 are also filled with carbon paste (not illustrated).

Both line sections 58, 60 extend behind the opening 24 within the sensor film 4 and can thus be wetted with the liquid sample via the said opening 24. The two line sections 58, 60 are electrically conductively connected by the liquid entering the opening 24, so that the conductivity of the liquid sample can be determined.

Figure 2:
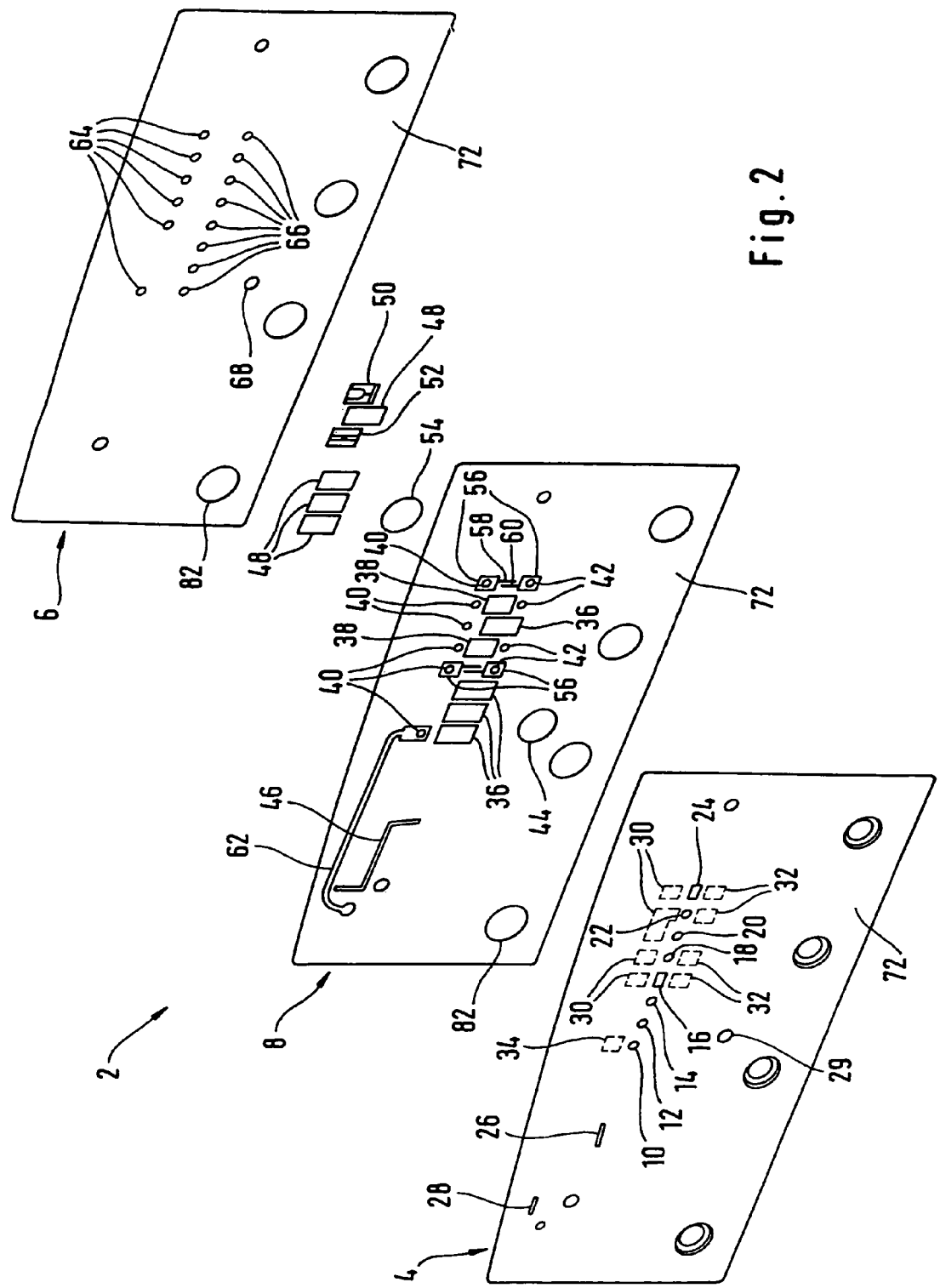
FIG. 2 shows a perspective exploded illustration of the sensor card from FIG. 1.

The method according to the invention will be explained below with reference to FIG. 2. Firstly, the films illustrated in FIG. 2, namely the sensor film 4, the covering film 6 and the intermediate film 8, are provided and arranged in the manner illustrated. Afterwards, the finished sensors or the parts of the sensors 48, 50, 52 that are still to be activated or operated later, which are formed as sensor inlays, are arranged in the corresponding cutouts 36, 38 in the intermediate film 8. Afterwards, the films 4, 6, 8 arranged one above the other are connected to one another in sheetlike fashion, in which case the connection may be effected by adhesive bonding, hot lamination, heat welding or radio frequency welding. The insertion of the sensors is configured in a particularly simple manner if the films 4, 6, 8 are already partially connected to one another prior to the insertion of the sensor inlays, for example by the lower edge 72 (FIG. 2) of the films 4, 6, 8 being incipiently laminated.

If only the carrier materials of still unfinished sensors are inserted into the cutouts, then the sensors are not activated or operated until after the connection of the films. For this purpose, the various analyte-specific reagent solutions for activation or operation of the sensors are applied through the openings in the sensor film onto the carrier materials of the respective sensors and dried.

What is claimed is:

1. A sensor card for determining analytes in liquid or gas samples with films connected to one another in sheetlike fashion, comprising:
   a sensor film with sample openings therethrough, the sensor film adapted to contact a sample;
   a planar covering film with electrical tapping openings therethrough, the covering film adapted to be remote from the sample;
   at least one intermediate film provided between the sensor film and the covering film, the intermediate film having at least one cutout; and
   at least one sensor comprising a carrier material, said carrier material arranged in the at least one cutout,
   wherein the sensor film, the at least one intermediate film, and the covering film are arranged one above the other in sheetlike fashion, and are connected by adhesive bonding, hot lamination, heat welding or radio frequency welding,
   wherein a thickness of the at least one intermediate film is greater than a thickness of the at least one sensor.

2. The sensor card according to claim 1, wherein the openings for electrical tapping are filled with a cured electrically conductive paste.

3. The sensor card according to claim 1, wherein the at least one sensor is an ion-selective sensor which may be electrically tapped via one of the electrical tapping openings in the covering film, and come into contact with a liquid or gas sample via one of the sample openings in the sensor film.

4. The sensor card according to claim 3, wherein the opening for electrical tapping in the covering film is arranged parallel to and offset with respect to the opening in the sensor film.

5. The sensor card according to claim 3, wherein the carrier material is activated with an ion-selective reagent mixture in the region of the sample opening in the sensor film.

6. The sensor card according to claim 5, wherein the carrier material has a conductive coating at its side facing the opening for electrical tapping.

7. The sensor card according to claim 1, wherein the sensor film has a plurality of printed-on electrical conductor tracks facing the at least one intermediate film, the conductor tracks being electrically tappable via the openings for electrical tapping and the at least one cutout in the intermediate film.

8. The sensor card according to claim 7, wherein the plurality of conductor tracks comprises a first conductor track and a second conductor track, and the at least one sensor is a gas sensor that is in contact with the first conductor track and the second conductor track on the sensor film and can contact a liquid or gas sample via one of the sample openings in the sensor film.

9. The sensor card according to claim 8, wherein the gas sensor is a carbon dioxide sensor.

10. The sensor card according to claim 9, wherein the carrier material comprises a coating facing the sensor film, which is an imprint made of silver chloride and a pH-sensitive material, there being applied on the coating an inner electrolyte and a gas-permeable membrane as activation.

11. The sensor card according to claim 8, wherein the gas sensor is an oxygen sensor.

12. The sensor card according to claim 11, wherein the oxygen sensor has layers of a material suitable as a working electrode and of a material suitable as a reference electrode; the layers being printed on the carrier material, there being applied on the layers an inner electrolyte and a gas-permeable membrane as activation.

13. The sensor card according to claim 7, wherein
   the plurality of conductor tracks comprises a first conductor track and a second conductor track, and
   the at least one sensor is a conductivity sensor having a first electrically conductive line section and a second electrically conductive line section which are spaced apart from one another and are printed on a side of the intermediate film which faces the sensor film,
   the first line section being in contact with the first conductor track on the sensor film and the second line section being in contact with the second conductor track on the sensor film and it being possible for the first and second line sections to be wetted by the liquid sample via a sample opening within the sensor film and to be electrically conductively connected.

14. The sensor card according to claim 1, further comprising a ventilation membrane that is arranged in the at least one cutout in the intermediate film, a first ventilation opening in the sensor film, and a second ventilation opening in the covering film, wherein the ventilation membrane adjoins the first ventilation opening in the sensor film and the second ventilation opening in the covering film.

15. The sensor card according to claim 1, wherein the at least one cutout in the intermediate film is elongated, the elongate cut-out being in flow connection with at least two separate sample openings in the sensor film.

16. The sensor card according to claim 15, wherein the two separate sample openings are elongated and run transversely at right angles to the elongate cut-out in the intermediate film.

17. The sensor card according to claim 1, further comprising a plate with at least one laterally open channel, the sensor film of the sensor card being fixed to the plate to form a laterally closed flow channel for the sample.

18. A method for producing a sensor card for determining analytes in liquid samples with films connected to one another in sheet-like fashion, the method comprising the steps of:
providing a sensor film with openings therethrough, a planar covering film with openings therethrough for electrical tapping, at least one intermediate film with at least one cutout, and at least one sensor comprising a carrier material,
arranging the carrier material in the at least one cutout; and
connecting the films arranged one above the other in sheetlike fashion, the intermediate film being arranged between sensor film and covering film, wherein the sensor film, the at least one intermediate film, and the covering film are connected by adhesive bonding, hot lamination, heat welding or radio frequency welding,
wherein a thickness of the at least one intermediate film is greater than a thickness of the at least one sensor.

19. The method according to claim 18, wherein at least one of the sensor film or covering film is partially connected to the at least one intermediate film in sheetlike fashion prior to arranging the sensor or the part of the sensor in the at least one cutout.

20. The method according to claim 19, wherein both the sensor film and the covering film are partially connected to the at least one intermediate film in sheetlike fashion prior to arranging the sensor or the part of the sensor in the at least one cutout.

21. The method according to claim 18, wherein, prior to providing the sensor film, conductor tracks are printed onto a side of the sensor film adapted to face the at least one intermediate film by screen printing.

22. The method according to claim 18, wherein, prior to providing the at least one intermediate film, line sections are printed onto a side of the intermediate film adapted to face the sensor film by screen printing.

23. The sensor card according to claim 1, wherein the entire at least one sensor is arranged in the at least one cutout of the intermediate layer.

24. The sensor card according to claim 1, wherein the electrical tapping openings extend perpendicular to a top surface of the planar covering film.

25. The sensor card according to claim 1, wherein at least one of the sensor film, the planar covering film, and the at least one intermediate film are polyester films.

26. The sensor card according to claim 1, wherein the thickness of each of the sensor film, the planar covering film, and the at least one intermediate film are between 80 and 120 µm.

27. The sensor card according to claim 5, wherein the carrier material is absorbent paper with a conductive coating.

28. A sensor card for determining analytes in liquid or gas samples with films connected to one another in sheetlike fashion, comprising:
a sensor film with sample openings therethrough, the sensor film adapted to contact a sample;
a planar covering film with electrical tapping openings therethrough, the covering film adapted to be remote from the sample;
at least one intermediate film provided between the sensor film and the covering film, the intermediate film having at least one cutout; and
at least one sensor comprising a carrier material, wherein the carrier material is an absorbent paper with a conductive coating, said carrier material arranged in the at least one cutout,
wherein the sensor film, the at least one intermediate film, and the covering film are arranged one above the other in sheetlike fashion, and are connected by adhesive bonding, hot lamination, heat welding or radio frequency welding.

29. A method for producing a sensor card for determining analytes in liquid samples with films connected to one another in sheet-like fashion, the method comprising the steps of:
providing a sensor film with openings therethrough, a planar covering film with openings therethrough for electrical tapping, at least one intermediate film with at least one cutout, and at least one sensor comprising a carrier material, wherein the carrier material is an absorbent paper with a conductive coating,
arranging the carrier material in the at least one cutout; and
connecting the films arranged one above the other in sheetlike fashion, the intermediate film being arranged between sensor film and covering film, wherein the sensor film, the at least one intermediate film, and the covering film are connected by adhesive bonding, hot lamination, heat welding or radio frequency welding.

* * * * *